United States Patent [19]

Cobb

[11] 4,420,431

[45] Dec. 13, 1983

[54] SALTS OF 3-CYANO-3-ALKENE-SULFINIC ACIDS AND SALTS OF 3-CARBAMOYL-3-ALKENE SULFONIC ACIDS AND PREPARATIONS THEREOF

[75] Inventor: Raymond L. Cobb, Bartlesville, Okla.

[73] Assignee: Phillips Petroleum Company, Bartlesville, Okla.

[21] Appl. No.: 11,744

[22] Filed: Feb. 13, 1979

[51] Int. Cl.³ .............. C07C 120/00; C07C 121/30; C07C 121/66; C07C 143/16

[52] U.S. Cl. .............................. 260/465.9; 260/464; 260/465 K; 260/465.6; 260/503; 260/507 R; 260/513 N; 526/222; 526/265

[58] Field of Search ............ 260/465.9, 464, 465.5 R, 260/465 E, 465.6, 513 N, 465 K, 503, 507 R

[56] References Cited

U.S. PATENT DOCUMENTS

| | | | |
|---|---|---|---|
| 2,312,878 | 3/1943 | Carpenter | 260/513 N |
| 2,330,713 | 9/1943 | Holbrook et al. | 260/513 N |
| 2,675,371 | 4/1954 | Coover, Jr. et al. | 260/465.9 X |
| 3,140,306 | 7/1964 | Heininger | 260/465 G |
| 3,213,125 | 10/1965 | Welcher | 260/465.9 X |
| 3,271,408 | 9/1966 | Frazza et al. | 260/465.9 X |
| 3,379,699 | 4/1968 | Stroh | 260/78.5 |
| 3,525,768 | 8/1970 | Hoke | 260/561 |
| 3,539,510 | 11/1970 | Priesing et al. | 210/52 |
| 3,541,119 | 11/1970 | Richter et al. | 260/464 X |
| 3,591,621 | 7/1971 | Hutchinson | 260/465.4 |
| 3,692,753 | 9/1972 | Smith et al. | 260/79.7 |
| 3,842,044 | 10/1974 | Cleary | 260/78 R |
| 3,848,000 | 11/1974 | Chabardes et al. | 260/465.9 X |
| 3,853,823 | 12/1974 | Cleary | 260/78 R |
| 3,922,250 | 11/1975 | Cleary | 260/49 |
| 3,931,118 | 1/1976 | Cleary | 260/78 SC |
| 3,951,923 | 4/1976 | Cleary | 260/78 A |
| 3,986,877 | 10/1976 | Timmerman et al. | 96/66.3 |

OTHER PUBLICATIONS

C.A.; vol. 76; 1972; Santilli, et al.; 46156c.
C.A.; vol. 80; 1974; Beck, et al.; 3439n.
C.A.; vol. 81; 1975; Ohta, et al.; 136970w.
C.A.; vol. 82; 1976; Gundermann, et al.; 57469g.

Primary Examiner—Joseph Paul Brust

[57] ABSTRACT

Novel sulfinates and sulfonates are provided comprising salts of 3-cyano-3-alkenesulfinic acids and salts of 3-carbamoyl-3-alkenesulfonic acids and process for preparing these novel compounds. The compounds of the invention are useful as comonomers or termonomers in the preparation of polymers, particularly polymers which are useful in fiber and textile applications.

11 Claims, No Drawings

SALTS OF 3-CYANO-3-ALKENE-SULFINIC ACIDS AND SALTS OF 3-CARBAMOYL-3-ALKENE SULFONIC ACIDS AND PREPARATIONS THEREOF

This invention relates to the production of new compositions of matter comprising sulfinates and sulfonates. In another aspect, this invention relates to novel cyanosulfinates and novel amidesulfonates. In accordance with another aspect, this invention relates to novel compositions of matter comprising salts of 3-cyano-3-alkenesulfinic acids and salts of 3-carbamoyl-3-alkenesulfonic acids. In accordance with a further aspect, this invention relates to a process for the production of 3-cyano-3-alkenesulfinic acids. In accordance with a further aspect, this invention relates to a process for the production of salts of 3-carbamoyl-3-alkenesulfonic acids by oxidation and hydrolysis of salts of 3-cyano-3-alkenesulfinic acids.

It is well known in the textile and fiber industries that functional groups on a polymer chain exhibit a great influence on the properties and the characteristics of the resultant polymers. Characteristics such as dyeability and dye-retention are the subject of a great deal of interest and activity in the fiber industry. Thus, materials which could be employed in the polymerization of monomers to form polymers with dye-receptive sites are of great interest. Such functional groups also frequently influence characteristics such as water absorption and solubility in polar solvents.

The present invention pertains to new compositions of matter comprising sulfinates and sulfonates which are useful as comonomers or termonomers in the preparation of polymers, particularly polymers which are useful in fiber and textile applications.

Accordingly, an object of this invention is to provide new compositions of matter.

A further object of this invention is to provide novel compositions which are useful as comonomers or termonomers in the preparation of polymers.

A further object of this invention is to provide a process for the production of the novel composition of the invention.

Other objects, aspects, as well as the several advantages of the invention, will be apparent to those skilled in the art upon reading the specification and the appended claims.

In accordance with the invention, novel sulfinates and sulfonates are provided comprising salts of 3-cyano-3-alkenesulfinic acids and salts of 3-carbamoyl-3-alkenesulfonic acids.

Further, in accordance with the invention, novel cyanosulfinates are formed by the reaction of sulfolenes with an alkali metal cyanide or quaternary ammonium cyanides in the presence of a solvent and a polyether.

Further, in accordance with the invention, novel amidesulfonates are formed by the hydrolysis and oxidation of salts of 3-cyano-3-alkenesulfinic acids.

In accordance with a further embodiment, sodium 3-cyano-3-butene-1-sulfinate, a new compound, is prepared in good yield by reaction of sodium cyanide with sulfolene in acetonitrile in the presence of a polyether. This salt is readily polymerizable with or without comonomers to give polymers with potentially dye-receptive pendant groups along the backbone of the polymer molecule.

The novel compositions of matter of this invention are generally referred to as salts of 3-cyano-3-alkenesulfinic acids and salts of 3-carbamoyl-3-alkenesulfonic acids which correspond to the following formulas I and II, respectively:

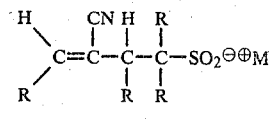

and

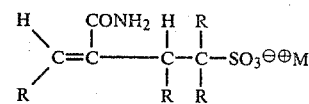

wherein the R groups are hydrogen or hydrocarbyl groups generally containing from 1 to 6 carbon atoms per group or alkoxy-substituted hydrocarbyl groups generally containing from 2 to 6 carbon atoms per group, with the further proviso that compounds of formula I or II contain a maximum of 12 carbon atoms per molecule and wherein M is an alkali metal or quaternary ammonium group of up to and including 6 carbon atoms.

Exemplary R groups suitable for compounds of formula I or II include hydrogen, methyl, ethyl, n-propyl, isopropyl, n-butyl, n-pentyl, n-hexyl, cyclopentyl, cyclohexyl, phenyl, methoxymethyl, ethoxymethyl, 1-methoxyethyl, 2-methoxyethyl, 3-isopropoxy-n-propyl, and the like. Exemplary M groups suitable for formulas I and II include lithium, sodium, potassium, rubidium, cesium, tetramethylammonium, and the like.

Specific novel compounds that have been prepared include sodium 3-cyano-3-butene-1-sulfinate and the corresponding sulfonate formed by oxidation of sodium 3-cyano-3-butene-1-sulfinate.

Compositions of formula I are prepared from compounds of formulas III or IV.

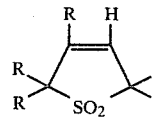   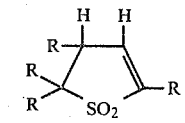

III                                  IV wherein the R groups are as defined above by reaction thereof with an alkali metal cyanide or quaternary ammonium cyanide in the presence of acetonitrile or tetrahydrofuran as solvent and polyethers.

The amount of acetonitrile or tetrahydrofuran employed in the preparation of compounds of formula I can vary within a broad range, for example, in amounts ranging from about 0.1 to 30, and preferably 1 to 10, parts by weight of sulfolene compound reactant (formulas III and IV) per 100 parts by weight of acetonitrile or tetrahydrofuran.

Examples of suitable compounds corresponding to formulas III or IV for use in preparing compounds of formula I include 2,5-dihydrothiophene-1,1-dioxide (beta-sulfolene), 2,3-dihydrothiophene-1,1-dioxide (alpha-sulfolene), and appropriately hydrocarbyl-substituted or alkoxyhydrocarbyl-substituted alpha- or beta-sulfolenes within the definitions given above for R groups.

The polyethers suitable for use in the preparation of the inventive compounds of formula I include cyclic and acyclic polyethers generally containing from 4 to 40 carbon atoms per molecule and 2 to 15 oxygen atoms per molecule. Examples of suitable polyethers include glyme, diglyme, triglyme, tetraglyme, and the like, and crown ethers, such as 12-crown-4, 15-crown-5, 18-crown-6, 24-crown-8, and the like. It is currently believed that the polyethers function in the reaction of cyanide compound with sulfolene compound by increasing the solubility of the cyanide compound in the organic solvent.

The amount of cyanide compound generally used in reaction with sulfolene compounds of formulas III and IV will be in the range of 0.5–5 moles of cyanide compound per mole of sulfolene compound, however, it is preferable to employ either stoichiometric amounts or a slight excess, for example, 1.0–1.5 moles of cyanide compound per mole of sulfolene compound.

The amount of polyether employed in the reaction of cyanide compounds with sulfolene compounds will generally be whatever is necessary to give the desired amount of product, however, from 0.005–3 parts by weight of polyether per part by weight of sulfolene compound is usually sufficient with 0.01–0.1 part by weight being preferred.

The temperature at which the reaction of cyanide compound with sulfolene compound is carried out can vary over a wide range depending, of course, upon the reactivity of the reactants and the desired degree of conversion of starting materials to products. Temperatures generally in the range of 0° to 100° C. are suitable, though it is preferred to employ temperatures in the range of 15° to 60° C. Likewise, the reaction time will be dependent upon reactivity of starting materials and desired degree of conversion. The reaction time will thus vary from several minutes to about one week. It will be recognized by one skilled in the art that, by analogy to acrylonitrile which polymerizes in the presence of a base, compounds of formula I would be expected to polymerize in the presence of cyanide ion; thus extended reaction time at elevated temperature should be avoided to prevent excessive polymerization of the desired product.

The novel compounds of this invention corresponding to formula II are readily prepared from compounds of formula I by hydrolysis of the nitrile group of formula I to the corresponding amide and oxidation of the sulfinate group of formula I to the sulfonate. The hydrolysis and oxidation steps can be performed separately or simultaneously. It is well within the skill of one knowledgeable in the field of organic chemistry to select agents and conditions to conduct the hydrolysis and oxidation reactions needed to convert the cyanosulfinates of formula I to the amidesulfonates of formula II. For example, air, oxygen gas, and like will cause the desired oxidation reaction. Reaction conditions are highly dependent upon the reactivity of the cyanosulfinate compound and the appropriate oxidizing agent. If desired, solvents of the type used in the preparation of the cyanosulfinates can also be used in the oxidation and hydrolysis of cyanosulfinate compound to sulfonates. Reaction temperatures will generally be in the range of 0° C. to 100° C. for whatever time is required to produce the desired degree of the conversion. It is preferred to conduct the hydrolysis and oxidation steps simultaneously, for example, by action of an aqueous solution of an oxidizing agent, such as, hydrogen peroxide.

Isolation and purification of the inventive compositions of matter can be accomplished by any of the means well known in the art, such as, filtration, recrystallization, solvent extraction, and the like.

The compounds of the invention are readily polymerizable or copolymerizable with a wide variety of comonomers to give polymers which can be used in the fiber and textile industries.

EXAMPLE

The following run illustrates the preparation of sodium 3-cyano-3-butene-1-sulfinate by reaction of β-sulfolene (2,5-dihydrothiophene-1,1-dioxide) and sodium cyanide in the presence of acetonitrile as solvent and 18-crown-6 [cyclic polyether of structure $-(CH_2-CH_2-O)_6-$].

A mixture of β-sulfolene (11.8 gm), sodium cyanide (5.9 gm), 18-crown-6 (0.25 gm) and acetonitrile (250 ml) under nitrogen atmosphere was stirred at room temperature (~20° C.) for 2½ days and than at 55° C. for 3 days. A pale cream-colored solid (17.0 gm) was isolated from the reaction mixture by filtration (under nitrogen atmosphere) followed by washing with acetonitrile, tetrahydrofuran and ether in sequence and then drying under vacuum at 50° C. In Table I are given analytical data on the thus-recovered solid.

TABLE I

Elemental analysis: Calculated for $C_5H_6NNaO_2S \cdot \frac{3}{4}Na\ CN \cdot \frac{1}{2}H_2O$:

|  | C | H | N | Na | S |
| --- | --- | --- | --- | --- | --- |
| Found | 32.43 | 3.32 | 11.51 | 18.90 | 15.06 |
|  | 32.9 | 3.8 | 10.1 | 15.8 | 13.8 |

Infrared absorption. 4.5 μ(—CN), 9.7 and 10.4μ ($-SO_2^-$).

$^1$H NMR[2]. 6–6.1 (broad doublet, $CH_2=$), 2.8(broad singlet, $-CH_2-CH_2-$).

$^{13}$C NMR[3]. 134.9 (triplet, $CH_2=$), 121.6(singlet, $=C<$), 59.4 (triplet, $-CH_2-SO_2$), 28.3(triplet, allylic $-CH_2-$).

(1) Major definitive absorbances measured in KBr pellet.
(2) Major absorbances (measured in D$_2$O) expressed in parts per million downfield from tetramethylsilane as an internal standard.
(3) Major absorbances (measured in D$_2$O) expressed in parts per million downfield from tetramethylsilane as an external standard.

The above analytical data revealed that the isolated solid was not a pure compound, but a mixture of compounds containing, among others, unreacted sodium cyanide and a major reaction product for which the analytical data are consistent with the structure

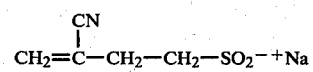

The major reaction product defied further attempts at purification without decomposition.

In order to verify the structure of the major reaction product, the above-described solid was subjected to oxidation conditions to convert the cyanosulfinate (major reaction product) to an amidesulfonate as described below.

The solid from the above (8 gm) was dissolved in water (30 ml) and slowly treated beginning at room temperature with excess 30% hydrogen peroxide (7 ml). The resulting solution was added slowly to a dispersion of 10% palladium on charcoal (0.25 gm) in water (50 ml) to destroy excess hydrogen peroxide. After filtration of the suspension, the filtrate was subjected to high vacuum to remove the water. The residual solid was redissolved in water (25 ml). Methanol was added until a cloud point was reached. Subsequent cooling to $-70°$ C. allowed a small amount of inorganic salt to be removed by filtration. The filtrate was poured into ethanol (500 ml) to separate another small amount of inorganic salt. Stripping of the resultant filtrate under high vacuum and washing of the resultant solid with a mixture of methanol and isopropanol followed by drying at 50° C. under vacuum gave a cream-colored solid (4.46 gm), analytical data of which are given in Table II.

TABLE II

Elemental Analysis. Calculated for $C_5H_8NNaO_4S\cdot\frac{1}{3}NaCN\cdot 2H_2O$:

|  | C | H | N | Na | S |
|---|---|---|---|---|---|
| Found | 25.26 | 4.77 | 7.37 | 12.10 | 12.65 |
|  | 25.7 | 3.7 | 5.5 | 13.2 | 13.7 |

Infrared absorption. 5.9 and 6.3μ ($CONH_2$), 8.3 and 9.5μ, ($-SO_3^{\ominus}$).

$^1$H NMR$^2$. 1.8–3.2 (broad multiplet), 5.6 (multiplet), 6.0 (singlet).

$^{13}$C NMR$^3$. 146.94 ($=C<$), 128.51 ($=CH_2$), 55.96 ($-CH_2-SO_3$), 33.68 (allylic $-CH_1-$).

(1) See footnote (1) in Table I.
(2) See footnote (2) in Table I.
(3) See footnote (3) in Table I.

The above data revealed an impure mixture of compounds with the major component being consistent with the structure

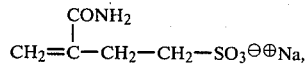

thus supporting the structure assignment for the major reaction product from the reaction of β-sulfolene and sodium cyanide.

I claim:

1. Salts of 3-cyano-3-alkenesulfinic acids which correspond to formula I

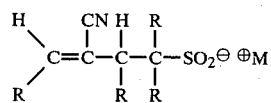

wherein the R groups are hydrogen or alkyl, cycloalkyl and phenyl groups containing from 1 to 6 carbon atoms per group or alkoxy-substituted alkyl and cycloalkyl groups containing from 2 to 6 carbon atoms per group, with the further proviso that compounds of formula I contain a maximum of 12 carbon atoms per molecule and wherein M is an alkali metal or quaternary ammonium group of up to and including 6 carbon atoms.

2. A salt of formula I according to claim 1 which is sodium 3-cyano-3-butene-1-sulfinate.

3. A process for the preparation of salts of 3-cyano-3-alkene-sulfinic acids according to claim 1 which comprises reacting a sulfolene with an alkali metal cyanide or quaternary ammonium cyanide in the presence of an inert solvent and a polyether under conditions which produce a compound of formula I.

4. A process according to claim 3 wherein the solvent is acetonitrile or tetrahydrofuran, said polyether is selected from cyclic and acyclic polyethers containing from 4 to 40 carbon atoms per molecule and 2 to 15 oxygen atoms per molecule.

5. A process according to claim 3 wherein the amount of cyanide present ranges from 0.5 to 5 moles per mole of sulfolene compound, the amount of polyether present ranges from 0.005 to 3 parts by weight of sulfolene compound, and the temperature in the range of about 0° to 100° C.

6. A process according to claim 3 for producing sodium 3-cyano-3-butenesulfinic acid which comprises reacting 2,5-dihydrothiophene-1,1-dioxide with sodium cyanide in the presence of acetonitrile and a cyclic polyether.

7. A mixture of compounds formed according to claim 3 containing as a major reaction product compounds of formula I.

8. Salts of 3-carbamoyl-3-alkenesulfonic acids which correspond to formula II

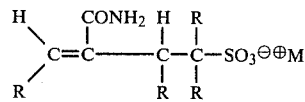

wherein the R groups are hydrogen or alkyl, cycloalkyl and phenyl groups containing from 1 to 6 carbon atoms per group or alkoxy-substituted alkyl and cycloalkyl groups containing from 2 to 6 carbon atoms per group, with the further proviso that compounds of formula II contain a maximum of 12 carbon atoms per molecule and wherein M is an alkali metal or quaternary ammonium group of up to and including 6 carbon atoms.

9. A compound according to claim 8 which is an amidesulfonate corresponding to the oxidized and hydrolyzed salt of sodium 3-cyano-3-butene-1-sulfonate.

10. A process for the conversion of cyanosulfinate compounds of formula I defined in claim 1 to the corresponding amidesulfonates which comprises hydrolyzing the nitrile group to the corresponding amide and oxidizing the sulfinate group to the sulfonate under conditions which produce sulfonates of formula II defined in claim 8.

11. A mixture of compounds formed according to claim 10 containing as a major reaction product compounds of formula II.

* * * * *